(12) United States Patent
Duval et al.

(10) Patent No.: US 9,365,489 B2
(45) Date of Patent: Jun. 14, 2016

(54) NITROOXY ALKANOIC ACIDS AND DERIVATIVES THEREOF IN FEED FOR REDUCING METHANE EMISSION IN RUMINANTS, AND/OR TO IMPROVE RUMINANT PERFORMANCE

(71) Applicant: DSM IP ASSETS B.V., Heerlen (NL)

(72) Inventors: Stephane Duval, Kaiseraugst (CH); Maik Kindermann, Kaiseraugst (CH)

(73) Assignee: DSM IP ASSETS B.V., Heerlen (NL)

( * ) Notice: Subject to any disclaimer, the term of this patent is extended or adjusted under 35 U.S.C. 154(b) by 7 days.

(21) Appl. No.: 14/159,576

(22) Filed: Jan. 21, 2014

(65) Prior Publication Data

US 2014/0134282 A1    May 15, 2014

Related U.S. Application Data

(62) Division of application No. 13/514,165, filed as application No. PCT/EP2010/069338 on Dec. 10, 2010, now Pat. No. 8,784,871.

(30) Foreign Application Priority Data

Dec. 11, 2009  (EP) .................................... 09178849
Aug. 6, 2010  (EP) .................................... 10172173

(51) Int. Cl.
| | | |
|---|---|---|
| *C07C 203/04* | (2006.01) | |
| *A23K 1/16* | (2006.01) | |
| *A23K 1/18* | (2006.01) | |
| *A61K 31/21* | (2006.01) | |
| *A61K 31/215* | (2006.01) | |
| *A61K 45/06* | (2006.01) | |
| *C07C 235/06* | (2006.01) | |

(52) U.S. Cl.
CPC ............. *C07C 203/04* (2013.01); *A23K 1/1603* (2013.01); *A23K 1/1609* (2013.01); *A23K 1/1813* (2013.01); *A61K 31/21* (2013.01); *A61K 31/215* (2013.01); *A61K 45/06* (2013.01); *C07C 235/06* (2013.01); *Y02P 60/56* (2015.11)

(58) Field of Classification Search
None
See application file for complete search history.

(56) References Cited

U.S. PATENT DOCUMENTS

| 6,638,929 | B2 * | 10/2003 | Berger et al. ............... 514/232.8 |
| 2006/0189603 | A1 * | 8/2006 | Garvey et al. ............... 514/223.2 |
| 2007/0149801 | A1 | 6/2007 | Rivolta et al. |
| 2009/0285931 | A1 * | 11/2009 | Shelby et al. ...................... 426/2 |
| 2010/0249189 | A1 | 9/2010 | Almirante et al. |

FOREIGN PATENT DOCUMENTS

| JP | 60-178845 | 9/1985 |
| JP | 05-504353 | 7/1993 |
| WO | WO 2005/054175 | 6/2005 |
| WO | WO 2009/098113 | 8/2009 |

OTHER PUBLICATIONS

Lazzarato et al. "Searching for New No-Donor Aspirin-like Molecules: A New Class of Nitrooxy-acyl Derivatives of Salicylic Acid" . J. Med. Chem. 2008 1894-1903.*
Zampolli et al. "Inhibition of Endothelial Cell Activation by Nitric Oxide Donors". The Journal of Pharmacology and Experimantal Therapeutics vol. 295, No. 2 2000. 818-823.*
International Search Report for PCT/EP2010/069338 mailed Mar. 8, 2011.
O. Piermatti et al., "Synthesis and Characterization of Carnitine Nitro-Derivatives", Bioorganic & Medicinal Chemistry, Oct. 22, 2007, vol. 16. No. 3, pp. 1444-1451.
Abstract—Hcaplus—2008:237525 Doc. # 148;417247 Lassarrato et al—Searching for New No-Donor Aspirin Like Molecules—& Article—J. of Med, Chem. 2008 51(6) 1894-1903.
Office Action dated Sep. 24, 2006.
Zampolli et al., "Inhibition of Endothelial Cell Activation by Nitric Oxide Donors", The Journal of Pharmacology and Experimental Therapeutics, Jun. 20, 2000, vol. 296. No. 2, pp. 818-823.

* cited by examiner

*Primary Examiner* — Robert A Wax
*Assistant Examiner* — Danah Al-Awadi
(74) *Attorney, Agent, or Firm* — Nixon & Vanderhye P.C.

(57) ABSTRACT

The present invention relates to a method for reducing the production of methane emanating from the digestive activities of a ruminant and or for improving ruminant animal performance by using, as active compound at least one nitrooxy alkanoic acid and/or derivative thereof, which is administrated to the animal together with the feed. The invention also relates to the use of these compounds in feed and feed additives such as premix, concentrates and total mixed ration (TMR) or in the form of a bolus.

14 Claims, No Drawings

NITROOXY ALKANOIC ACIDS AND DERIVATIVES THEREOF IN FEED FOR REDUCING METHANE EMISSION IN RUMINANTS, AND/OR TO IMPROVE RUMINANT PERFORMANCE

This application is a divisional of commonly owned copending U.S. application Ser. No. 13/514,165, filed Aug. 20, 2012 (now U.S. Pat. No. 8,784,871), which is the U.S. national phase of International Application No. PCT/EP2010/069338, filed Dec. 10, 2010 which designated the U.S. and claims priority to EP 09178849.7, filed Dec. 11, 2009 and EP 10172173.6, filed Aug. 6, 2010, the entire contents of each of which are hereby incorporated by reference.

The present invention relates to the use of at least one nitrooxy alkanoic acid and/or derivative thereof for reducing the production of methane emanating from the digestive activities of ruminants, and/or to improve the ruminant performance.

The present invention also relates to animal feed or animal feed composition and feed additives comprising these above mentioned compounds. The term feed or feed composition means any compound, preparation, mixture, or composition suitable for, or intended for intake by an animal.

In the present context, a ruminant is a mammal of the order Artiodactyla that digests plant-based food by initially softening it within the animal's first stomach, known as the rumen, then regurgitating the semi-digested mass, now known as cud, and chewing it again. The process of again chewing the cud to further break down plant matter and stimulate digestion is called "ruminating". Ruminating mammals include cattle, goats, sheep, giraffes, American Bison, European bison, yaks, water buffalo, deer, camels, alpacas, llamas, wildebeest, antelope, pronghorn, and nilgai.

For all embodiments of the present invention, domestic cattle, sheep and goat are the more preferred species. For the present purposes most preferred species are domestic cattle. The term includes all races of domestic cattle, and all production kinds of cattle, in particular dairy cows and beef cattle.

Rumen fermentation brings some disadvantages. Methane is produced as a natural consequence of the anaerobic fermentation, which represents an energy loss to the host animal. Carbohydrate makes up 70 to 80% of the dry matter in a typical dairy cattle ration and in spite of this the absorption of carbohydrates from the gastrointestinal tract is normally very limited. The reason for this is the extensive fermentation of carbohydrates in the rumen resulting in production of acetate, propionate and butyrate as the main products. These products are part of the so called volatile fatty acids, (VFAs).

Besides the energy loss, methane is also a greenhouse gas, which is many times more potent than $CO_2$. Its concentration in the atmosphere has doubled over the last century and continues to increase alarmingly. Ruminants are the major contributors to the biogenic methane formation, and it has been estimated that the prevention of methane formation from ruminants would almost stabilize atmospheric methane concentrations.

Furthermore, the assessment of the Kyoto protocol places increased priority in decreasing methane emissions as part of a multi-gas strategy. The most effective additives currently used for reducing the formation of methane contain antibiotics which diminish the proliferation of microorganisms providing hydrogen ($H_2$) to the methanogenes. However, the effect of antibiotics on the formation of methane has some disadvantages because of rapid adaptation of the microflora and/or resistance development leading to a complete loss of the intended effect within a short period of time (2 to 3 weeks).

In recent years there has been an intense debate about the use of antibiotics in animal feed and in many countries a ban on this type of additions to feed additives is being considered or already in place.

Non antibiotic products (bile acid derivatives) leading to reduction of methane emission when tested using an in vitro rumen simulation model have recently been published (WO2010072584). However, the amount required to produce a moderate reduction of methane emission are not compatible with the ruminant feed industry cost constraints. Furthermore, a number of natural plant extracts (Garlic WO2009150264, yucca, cinnamon, rhubarb . . . ) have been described in the scientific literature as potent solutions to reduce methane emission in ruminants based on in vitro experiments. However, none of these made it to a commercial product because of side effects (residues in milk), or lack efficacy, when tested in vivo.

Under these circumstances there is a need to develop new substances which reduce the formation of methane and which are in line with reliable and generally accepted practice and not of a medicinal nature. In addition to reducing methane emission, such substances may also contribute to improve ruminant performance by improving the feed conversion ratio, reducing feed intake, improving weight gain, and/or improving carcass, or milk yield.

The present inventors surprisingly found that the compounds specified herein after have a great potential for use in animal feed in order to essentially reduce the formation of methane without affecting microbial fermentation in a way that would be detrimental to the host animal. Moreover, the compounds of the present invention have also a great benefit regarding overall animal performance as measured by feed conversion ratio, feed intake, weight gain, carcass yield, or milk yield. Said compounds are also more stable than those described in the prior art, safer for the animal and human, lead to persistent methane reduction effect, they do not affect palatability, they can be produced at industrial scale at a cost compatible with the animal nutrition industry, and above all, they do not provoke accumulation of any metabolite in the milk or meat of the treated animal.

In particular, it has been observed that the addition of at least one nitrooxy alkanoic acid and/or derivative thereof according to the invention is highly effective in decreasing methane formation in in vitro experiments without affecting total VFA production, and in decreasing overall methane production in vivo.

Therefore, the present invention provides the use of at least one nitrooxy alkanoic acid and/or derivative thereof as defined by formula (I) as an active compound in animal feeding for reducing the formation of methane emanating from the digestive activities of ruminants and/or for improving ruminant performance.

The invention further provides a method for reducing the production of methane emanating from the digestive activities of ruminants and/or improving ruminant animal performance, comprising orally administering a sufficient amount of at least one nitrooxy alkanoic acid and/or derivative thereof as defined by formula (I) to the animal.

In all embodiments of the present invention, nitrooxy alkanoic acids and/or derivatives thereof are defined by the following formula (I)

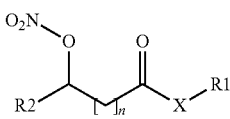

formula (I)

wherein n is comprised between 0 and 23, preferably between 0 and 9, and wherein, if n≠0, the carbon chain is a linear, a cyclic, or a branched linear or cyclic aliphatic carbon chain which may be mono- or polyunsaturated and in any isomeric form, X is independently O, NH, or N—R3, wherein if R1≠H, X—R1- represents an ester or a secondary amide derivative, R1 is independently, hydrogen or a saturated straight, cyclic or branched chain of an alkyl or alkenyl group containing 1 to 10, preferably 1 to 5 carbon atoms, R2 is independently, hydrogen or a saturated straight or branched chain of an alkyl or alkenyl group containing 1 to 23, preferably 1 to 9 carbon atoms, and R3 is independently, hydrogen or a saturated straight, cyclic or branched chain of an alkyl or alkenyl group containing 1 to 10, preferably 1 to 5 carbon atoms.

It is to be understood in the above definition of compounds of formula (I) that when n>2, the carbon chain can be linear or branched at any position along the carbon chain. In addition, the carbon chain can be branched by multiple branches at different positions along the carbon chain. Moreover, when n>4, the aliphatic carbon chain may form a cyclic moiety. This cycloalkyl-carboxylate moiety can carry the nitrooxy moiety at position 2, 3, 4, and it can also be branched at multiple positions by any aliphatic groups. The branched aliphatic groups are preferably, methyl, ethyl or propyl.

In the above definition of derivatives of the formula (I) a preferred alkyl group is methyl, ethyl, propyl, isopropyl, butyl, sec. butyl, isobutyl, pentyl, neopentyl, hexyl, cyclohexyl, and 2-ethyl-hexyl and octyl. Furthermore any alkyl or alkenyl group containing three or more carbon atoms can be straight chain, branched, or cyclic. In addition for the straight chain or branched $C_2$-$C_{10}$-alkenylene group, this is understood to encompass alkenylene groups with one or (from $C_4$) more double bonds; examples of such alkenylene groups are those of the formulae —CH=CH—, —CH=CH—$CH_2$—, —CH=CH—$(CH_2)_3$— and —$(CH=CH)_2$—.

In a particular embodiment, preferred esters according to the present invention are methyl, ethyl, propyl, isopropyl, butyl, sec. butyl, isobutyl, pentyl, neopentyl, hexyl, 2-ethyl-hexyl and octyl. Moreover, preferred amide derivatives are methyl-amide, ethyl-amide, propyl-amide, butyl-amide, pentyl-amide, dimethyl-amide, diethylamide, and methyl-ethyl-amide.

In another embodiment, more preferred derivatives of formula (I) are derivatives, wherein n is comprised between 0 and 23, preferably between 0 and 9, and wherein, if n≠0, the carbon chain is a linear, a cyclic, or branched linear or cyclic aliphatic carbon chain which may be mono- or polyunsaturated and in any isomeric form, X is independently O, NH, or N—R3, wherein if R1≠H, X—R1- represents an ester or a secondary amide derivative, and R1, R2, and R3 are all three independently a hydrogen, a methyl, or an ethyl group.

In another embodiment, even more preferred compounds are derivatives, wherein n is comprised between 0 and 23, preferably between 0 and 9, and wherein, if n≠0, the carbon chain is a linear, a cyclic, or branched linear or cyclic aliphatic carbon chain which may be mono- or polyunsaturated and in any isomeric form, X is independently O, NH, or N—R3, wherein if R1≠H, X—R1- represents an ester or a secondary amide derivative, and R2 is a hydrogen.

In another embodiment, even more preferred compounds are derivatives, wherein n is comprised between 0 and 23, preferably between 0 and 9, and wherein, if n≠0, the carbon chain is a linear, a cyclic, or branched linear or cyclic aliphatic carbon chain which may be mono- or polyunsaturated and in any isomeric form, X is oxygen (O), wherein if R1≠H, X—R1- represents an ester, and R2 is a hydrogen.

In yet another embodiment, more preferred derivatives of formula (I) are selected from the group consisting of: nitrooxy ethanoic acid, 3-nitrooxy propionic acid, 4-nitrooxy butanoic acid, 5-nitrooxy pentanoic acid, 6-nitrooxy hexanoic acid, 7-nitrooxy heptanoic acid, 2-nitrooxy-cyclohexylcarboxylic acid, 3-nitrooxy-cyclohexylcarboxylic acid, 4-nitrooxy-cyclohexylcarboxylic acid, 8-nitrooxy octanoic acid, 9-nitrooxy nonanoic acid, 10-nitrooxy decanoic acid, 11-nitrooxy undecanoic acid, methyl-nitrooxy ethanoate, methyl-3-nitrooxy propionate, methyl-4-nitrooxy butanoate, methyl-5-nitrooxy pentanoate, methyl-6-nitrooxy hexanoate, methyl-7-nitrooxy heptanoate, methyl-2-nitrooxy-cyclohexylcarboxylate, methyl-3-nitrooxy-cyclohexylcarboxylate, methyl-4-nitrooxy-cyclohexylcarboxylate, methyl-8-nitrooxy octanoate, methyl-9-nitrooxy nonanoate, methyl-10-nitrooxy decanoate, methyl-11-nitrooxy undecanoate, ethyl-nitrooxy ethanoate, ethyl-3-nitrooxy propionate, ethyl-4-nitrooxy butanoate, ethyl-5-nitrooxy pentanoate, ethyl-6-nitrooxy hexanoate, ethyl-7-nitrooxy heptanoate, ethyl-2-nitrooxy-cyclohexylcarboxylate, ethyl-3-nitrooxy-cyclohexylcarboxylate, ethyl-4-nitrooxy-cyclohexylcarboxylate, ethyl-8-nitrooxy octanoate, ethyl-9-nitrooxy nonanoate, ethyl-10-nitrooxy decanoate, ethyl-11-nitrooxy undecanoate, nitrooxy-N-ethanoic amide, nitrooxy-N-methyl-ethanoic amide, nitrooxy-N-dimethyl-ethanoic amide, nitrooxy-N-ethyl-ethanoic amide, nitrooxy-N-diethyl-ethanoic amide, nitrooxy-N-methyl-ethyl-ethanoic amide, 3-nitrooxy-N-propionic amide, 3-nitrooxy-N-methyl-propionic amide, 3-nitrooxy-N-dimethylpropionic amide, 3-nitrooxy-N-ethyl-propionic amide, 3-nitrooxy-N-diethyl-propionic amide, 3-nitrooxy-N-methyl-ethyl-propionic amide, 4-nitrooxy-N-butanoic amide, 4-nitrooxy-N-methyl-butanoic amide, 4-nitrooxy-N-dimethyl-butanoic amide, 4-nitrooxy-N-ethyl-butanoic amide, 4-nitrooxy-N-diethyl-butanoic amide, 4-nitrooxy-N-methyl-ethyl-butanoic amide, 5-nitrooxy-N-pentanoic amide, 5-nitrooxy-N-methyl-pentanoic amide, 5-nitrooxy-N-dimethyl-pentanoic amide, 5-nitrooxy-N-ethyl-pentanoic amide, 5-nitrooxy-N-diethyl-pentanoic amide, 5-nitrooxy-N-methyl-ethylpentanoic amide, 6-nitrooxy-N-pentanoic amide, 6-nitrooxy-N-methyl-pentanoic amide, 6-nitrooxy-N-dimethyl-pentanoic amide, 6-nitrooxy-N-ethyl-pentanoic amide, 6-nitrooxy-N-diethyl-pentanoic amide, 6-nitrooxy-N-methyl-ethyl-pentanoic amide, 2-nitrooxy propionic acid, methyl-2-nitrooxy propionate, ethyl-2-nitrooxy propionate, 2-nitrooxy butanoic acid, methyl-2-nitrooxy butanoate, ethyl-2-nitrooxy butanoate, 3-nitrooxy butanoic acid, methyl-3-nitrooxy butanoate, ethyl-3-nitrooxy butanoate, 2,2-dimethyl-3-nitrooxy propionic acid, methyl-2,2-dimethyl-3-nitrooxy propionate, and ethyl-2,2-dimethyl-3-nitrooxy propionate.

In the above definition of derivatives of the formula (I), most preferred derivatives or of formula (I) for all the embodiments of the present invention, and in view of their properties in decreasing methane produced by ruminants are selected from the group consisting of: ethyl-nitrooxy-ethanoate, 3-nitrooxy propionic acid, methyl-3-nitrooxy propionate, ethyl-3-nitrooxy propionate, ethyl-2-nitrooxy propanoate, 4-nitrooxy butanoic acid, ethyl-4-nitrooxy-butanoate, ethyl-3-nitrooxy-butanoate, 5-nitrooxy pentanoic acid, ethyl-5-nitrooxy pentanoate, 2,2-dimethyl-3-nitrooxy propionic acid, 6-nitrooxy hexanoic acid, ethyl-6-nitrooxy hexanoate, 8-nitrooxy octanoic acid, ethyl-8-nitrooxy octanoate, 11-nitrooxy undecanoic acid, ethyl-11-nitrooxy undecanoate, ethyl-4-nitrooxy-cyclohexylcarboxylate, 5-nitrooxy-N-pentanoic amide, and 5-nitrooxy-N-methyl-pentanoic amide, which chemical structures are shown in Table 1.

TABLE 1

| Most preferred derivatives according to the present invention | |
|---|---|
| [structure] | 3-nitrooxy propionic acid |
| [structure] | methyl-3-nitrooxy propionate |
| [structure] | Ethyl-3-nitrooxy propionate |
| [structure] | Ethyl-4-nitrooxy butanoate |
| [structure] | Ethyl-3-nitrooxy butanoate |
| [structure] | 5-nitrooxy pentanoic acid |
| [structure] | Ethyl-5-nitrooxy pentanoate |
| [structure] | 6-nitrooxy hexanoic acid |
| [structure] | Ethyl-6-nitrooxy hexanoate |
| [structure] | ethyl-4-nitrooxy-cyclohexylcarboxylate |
| [structure] | 8-nitrooxy octanoic acid |
| [structure] | Ethyl-8-nitrooxy octanoate |

TABLE 1-continued

Most preferred derivatives according to the present invention

| Structure | Name |
|---|---|
| O₂N–O–(CH₂)₉–C(=O)–OH | 11-nitrooxy undecanoic acid |
| O₂N–O–(CH₂)₉–C(=O)–O–CH₂CH₃ | Ethyl-11-nitrooxy undecanoate |
| O₂N–O–(CH₂)₄–C(=O)–NH₂ | 5-nitrooxy-pentanoic amide |
| O₂N–O–(CH₂)₄–C(=O)–NH–CH₃ | 5-nitrooxy-N-methyl-pentanoic amide |

Even more preferred derivatives or of the formula (I) are selected from the group consisting of: 3-nitrooxy propionic acid, methyl-3-nitrooxy propionate, ethyl-3-nitrooxy propionate, ethyl-4-nitrooxy-butanoate, ethyl-3-nitrooxy-butanoate, 5-nitrooxy pentanoic acid, ethyl-5-nitrooxy pentanoate, 6-nitrooxy hexanoic acid, ethyl-6-nitrooxy hexanoate, ethyl-4-nitrooxy-cyclohexylcarboxylate, 8-nitrooxy octanoic acid, ethyl-8-nitrooxy octanoate, 11-nitrooxy undecanoic acid, ethyl-11-nitrooxy undecanoate, 5-nitrooxy-pentanoic amide, and 5-nitrooxy-N-methyl-pentanoic amide.

The term "a derivative thereof" as used herein also comprises salts of the nitrooxy alkanoic acids. Preferred cations for salt preparation may be selected from the group consisting of sodium (Na+), potassium (K+), lithium (Li+), magnesium (Mg2+), calcium (Ca2+), barium (Ba2+), strontium (Sr2+), and ammonium (NH4+). Salts may also be prepared from an alkali metal or an alkaline earth metal.

The compounds of the present invention can be manufactured in principle according to synthetic methods known per se for nitrooxy alkanoic acids, esterifications or amidations.

In all these cases appropriate methods to purify the product (compounds of formula (I)) can be chosen by those skilled in the art, i.e. by column chromatography, or the compound of formula (I), can be isolated and purified by methods known per se, e.g. by adding a solvent such as diethyl-ether or ethyl acetate to induce the separation of the crude product from the mixture after reaction, and drying over $Na_2SO_4$ of the collected crude product.

Methane emission by ruminants can easily be measured in individual animals in metabolic chambers by methods known in the art (Grainger et al., 2007 J. Dairy Science; 90: 2755-2766). Moreover, it can also be assessed at barn level by an emerging technology using laser beam (McGinn et al., 2009, Journal of Environmental Quality; 38: 1796-1802). Alternatively, methane produced by a dairy ruminant can also be assessed by measurement of VFA profiles in milk according to WO 2009/156453.

Ruminant performance can be assessed by methods well known in the art, and is usually characterized by feed conversion ratio, feed intake, weight gain, carcass yield, or milk yield.

The present invention also relates to the use of at least one nitrooxy alkanoic acid and/or derivative thereof in combination with at least one additional active substance which shows similar effects with regard to methane formation in the rumen and which is selected from the group consisting of diallyl disulfide, garlic oil, allyl isothiocyanate, deoxycholic acid, chenodeoxycholic acid and derivatives thereof.

Further components that could be given together with the compound according to the present invention are for example yeasts, essential oils, and ionophores like Monensin, Rumensin.

It is at present contemplated that diallyl disulfide, garlic oil, allyl isothiocyanate deoxycholic acid, chenodeoxycholic acid and derivatives thereof are independently administered in dosage ranges of for example 0.01 to 500 mg active substance per kg feed (ppm). These compounds are either commercially available or can easily be prepared by a skilled person using processes and methods well-known in the prior art.

The present invention also relates to the use of at least one nitrooxy alkanoic acid and/or derivative thereof, wherein the methane production in ruminants calculated in liters per kilogram of dry matter intake is reduced by at least 10% when measured in metabolic chambers. Preferably, methane reduction is at least 15%, more preferably, at least 20%, even more preferably, at least 25%, most preferably, at least 30%. Alternative methane emission measurements may also be used like using a laser beam or for dairy ruminants, correlating methane production to the VFA profile in milk.

The present invention also relates to the use of at least one nitrooxy alkanoic acid and/or derivative thereof, wherein the ruminant feed conversion ratio is reduced by least 1% when measured in conventional performance trial. Preferably, the feed conversion ratio is reduced by at least 2%, more preferably, by at least 2.5%, even more preferably, by at least 3%, most preferably, by at least 3.5%.

The present invention also relates to the use of at least one nitrooxy alkanoic acid and/or derivative thereof, wherein the amount of the at least one active compound as defined in formula (I) administered to the ruminant animal is from 1 mg to 10 g per kg of feed, preferably from 10 mg to 1 g per Kg of feed, more preferably, from 50 mg to 500 mg per kg of feed. For the use in animal feed, however, nitrooxy alkanoic acids and derivatives thereof need not be that pure; it may e.g. include other compounds and derivatives.

As indicated above, the compounds of the present invention are useful as compounds for feed additives and animal feed compositions for ruminants, and accordingly are useful as the active ingredients in such feed to reduce methane formation in the digestive tract of the animal, and or to improve ruminant performance.

For the realisation of their use as such ingredients for the feed of ruminants the compounds may be incorporated in the feed by methods known per se in the art of feed formulation and processing.

Further aspects of the present invention are therefore formulations, i.e. feed additives and animal feed compositions containing compounds as herein above defined. The normal daily dosage of a compound according to the invention provided to an animal by feed intake depends upon the kind of animal and its condition. Normally this dosage should be in the range of from about 1 mg to about 10 g, preferably from about 10 mg to about 1 g, more preferably, 50 mg to 500 mg compound per kg of feed.

The at least one nitrooxy alkanoic acid and/or derivative thereof may be used in combination with conventional ingredients present in an animal feed composition (diet) such as calcium carbonates, electrolytes such as ammonium chloride, proteins such as soya bean meal, wheat, starch, sunflower meal, corn, meat and bone meal, amino acids, animal fat, vitamins and trace minerals.

Particular examples of compositions of the invention are the following:
  An animal feed additive comprising (a) at least one compound selected from table 1 and (b) at least one fat-soluble vitamin, (c) at least one water-soluble vitamin, (d) at least one trace mineral, and/or (e) at least one macro mineral;
  An animal feed composition comprising at least one compound selected from table 1 and a crude protein content of 50 to 800 g/kg feed.

The so-called premixes are examples of animal feed additives of the invention. A premix designates a preferably uniform mixture of one or more micro-ingredients with diluents and/or carrier. Premixes are used to facilitate uniform dispersion of micro-ingredients in a larger mix.

Apart from the active ingredients of the invention, the premix of the invention contains at least one fat-soluble vitamin, and/or at least one water soluble vitamin, and/or at least one trace mineral, and/or at least one macro mineral. In other words, the premix of the invention comprises the at least one compound according to the invention together with at least one additional component selected from the group consisting of fat-soluble vitamins, water-soluble vitamins, trace minerals, and macro minerals.

Macro minerals may be separately added to the feed. Therefore, in a particular embodiment, the premix comprises the active ingredients of the invention together with at least one additional component selected from the group consisting of fat-soluble vitamins, water-soluble vitamins, and trace-minerals.

The following are non-exclusive lists of examples of these components:
  Examples of fat-soluble vitamins are vitamin A, vitamin D3, vitamin E, and vitamin K, e.g. vitamin K3.
  Examples of water-soluble vitamins are vitamin B12, biotin and choline, vitamin B1, vitamin B2, vitamin B6, niacin, folic acid and panthothenate, e.g. Ca-D-panthothenate.
  Examples of trace minerals are manganese, zinc, iron, copper, iodine, selenium, and cobalt.
  Examples of macro minerals are calcium, phosphorus and sodium.

As regards feed compositions for ruminants such as cows, as well as ingredients thereof, the ruminant diet is usually composed of an easily degradable fraction (named concentrate) and a fiber-rich less readily degradable fraction (named hay, forage, or roughage).

Hay is made of dried grass, legume or whole cereals. Grasses include among others timothy, ryegrasses, fescues. Legumes include among others clover, lucerne or alfalfa, peas, beans and vetches. Whole cereals include among others barley, maize (corn), oat, sorghum. Other forage crops include sugarcane, kales, rapes, and cabbages. Also root crops such as turnips, swedes, mangles, fodder beet, and sugar beet (including sugar beet pulp and beet molasses) are used to feed ruminants. Still further crops are tubers such as potatoes, cassava and sweet potato. Silage is an ensiled version of the fiber-rich fraction (e.g. from grasses, legumes or whole cereals) whereby material with a high water content is treated with a controlled anaerobic fermentation process (naturally-fermented or additive treated).

Concentrate is largely made up of cereals (such as barley including brewers grain and distillers grain, maize, wheat, sorghum), but also often contain protein-rich feed ingredients such as soybean, rapeseed, palm kernel, cotton seed and sunflower.

Cows may also be fed total mixed rations (TMR), where all the dietary components, e.g. forage, silage and concentrate, are mixed before serving.

As mentioned above a premix is an example of a feed additive which may comprise the active compounds according to the invention. It is understood that the compounds may be administered to the animal in different other forms. For example the compounds can also be included in a bolus that would be placed in the rumen and that would release a defined amount of the active compounds continuously in well defined dosages over a specific period of time.

The present invention further relates to a method for reducing the production of methane emanating from the digestive activities of a ruminant animal and/or for improving ruminant animal performance comprising orally administering a sufficient amount of at least one active compound as defined in formula (I) with preferred embodiments described for the derivatives.

Moreover, the invention further relates to a method as described above, wherein the active compound is administered to the animal in combination with at least one additional active substance selected from the group consisting of diallyl disulfide, garlic oil, allyl isothiocyanate, deoxycholic acid, chenodeoxycholic acid and derivatives thereof.

The invention also relates to a method as described above, wherein the ruminant animal is selected from the group consisting of: cattle, goats, sheep, giraffes, American Bison, European bison, yaks, water buffalo, deer, camels, alpacas, llamas, wildebeest, antelope, pronghorn, and nilgai, and more preferably from the group consisting of: cattle, goat and sheep.

The invention also relates to a method as described above, wherein the amount of the at least one active compound as defined in formula (I) administered to the ruminant animal is from about 1 mg to about 10 g per kg feed, preferably from about 10 mg to about 1 g, more preferably from 50 mg to 500 mg compound per kg of feed.

The invention also relates to a method as described above, wherein the methane production in ruminants calculated in liters per kilogram of dry matter intake is reduced by at least 10% when measured in metabolic chambers. Preferably, methane reduction is at least 15%, more preferably, at least 20%, even more preferably, at least 25%, most preferably, at least 30%. Alternative methane emission measurements may also be used like using a laser beam or for dairy ruminants, correlating methane production to the VFA profile in milk.

The invention also relates to a method as described above, wherein the ruminant feed conversion ratio is reduced by least 1% when measured in conventional performance trial. Preferably, the feed conversion ratio is reduced by at least 2%, more preferably, by at least 2.5%, even more preferably, by at least 3%, most preferably, by at least 3.5%.

The present invention is further described by the following examples which should not be construed as limiting the scope of the invention.

EXAMPLES

Example 1

In Vitro Test for Methane Production

A modified version of the "Hohenheim Forage value Test (HFT)" was used for testing the effect of specific compounds on the rumen functions mimicked by this in-vitro system.
Principle:
   Feed is given into a syringe with a composition of rumen liquor and an appropriate mixture of buffers. The solution is incubated at 39° C. After 8 hours the quantity (and composition) of methane produced is measured and put into a formula for conversion.
Reagents:
Mass Element Solution:
   6.2 g potassium dihydrogen phosphate ($KH_2PO_4$)
   0.6 g magnesium sulfate heptahydrate ($MgSO_4*7H_2O$)
   9 ml concentrated phosphoric acid (1 mol/l)
   dissolved in distilled water to 1 l (pH about 1.6)
Buffer Solution:
   35.0 g sodium hydrogen carbonate ($NaHCO_3$)
   4.0 g ammonium hydrogen carbonate (($NH_4)HCO_3$)
   dissolved in distilled water to 1 l
Trace Element Solution:
   13.2 g calcium chloride dihydrate ($CaCl_2*2H_2O$)
   10.0 g manganese(II) chloride tetrahydrate ($MnCl_2*4H_2O$)
   1.0 g cobalt(II) chloride hexahydrate ($CoCl_2*6H_2O$)
   8.0 g iron(III) chloride ($FeCl_3*6H_2O$)
   dissolved in distilled water to 100 ml
Sodium Salt Solution:
   100 mg sodium salt
   dissolved in distilled water to 100 ml
Reduction Solution:
   first 3 ml sodium hydroxide (c=1 mol/l), then 427.5 mg sodium sulfide hydrate ($Na_2S*H_2O$) are added to 71.25 ml $H_2O$
   solution must be prepared shortly before it is added to the medium solution
Procedure:
Sample Weighing:
   The feed stuff is sieved to 1 mm—usually TMR (44% concentrate, 6% hay, 37% maize silage and 13% grass silage)—and weighed exactly into 64 syringes. 4 of these syringes are the substrate controls, which display the gas production without the effect of the tested compounds. 4 other syringes are positive control, in which bromoethane sulfonate has been added to 0.1 mM. When needed, 4 syringes contain a carrier control (if the test compounds need a carrier). The remaining syringes contain the test substances, by groups of 4 syringes.
Preparation of the Medium Solution:
   The components are mixed in a Woulff bottle in following order:
   711 ml water
   0.18 ml trace element solution
   355.5 ml buffer solution
   355.5 ml mass element solution
   The completed solution is warmed up to 39° C. followed by the addition of 1.83 ml sodium salt solution and the addition of reduction solution at 36° C. The rumen liquor is added, when the indicator turns colourless.
Extraction of the Rumen Liquor:
   750 ml of rumen liquor are added to approximately 1,400 ml of medium solution under continued agitation and $CO_2$-gassing.
Filling the Syringes, Incubation and Determining Gas Volumes and VFA Values:
   The diluted rumen fluid (24 ml) is added to the glass syringe. The syringes are then incubated for 8 hours at 39° C. under gentle agitation. After 8 hours, the volume of gas produced is measured, and the percentage of methane in the gas phase is determined by gas chromatography.
Results
   The food fermented was artificial TMR (44% concentrate, 6% hay, 37% maize silage and 13% grass silage). The compounds produced as described in examples 3 to 20 were added to the fermentation syringes to a concentration of 2 to 0.01% of dry matter (DM). The results are presented in the following table.

TABLE 2

Methane reduction effect resulting from the average of two experiments with some compounds according to the present invention (a minus sign followed by an integer in the column effect on methanogenesis (%) means a reduction in methane produced when compared to control; no value means that the concentration was not tested)

| Structure | effect on methanogenesis (%) | | | | | | |
| --- | --- | --- | --- | --- | --- | --- | --- |
| | 2% DM | 1% DM | 0.5% DM | 0.25% DM | 0.1% DM | 0.05% DM | 0.01% DM |
| $O_2N\diagdown O\diagup\diagdown C(=O)\diagdown O\diagup\diagdown$ (ethyl nitrooxyacetate) | | | | | −1 | −1 | |
| $O_2N\diagdown O\diagup\diagdown\diagup C(=O)\diagdown O\diagup\diagdown$ (ethyl 3-nitrooxypropanoate) | −100 | −100 | −100 | −100 | −63 | −18 | |

TABLE 2-continued

Methane reduction effect resulting from the average of two experiments
with some compounds according to the present invention (a minus sign followed by
an integer in the column effect on methanogenesis (%) means a reduction in methane
produced when compared to control; no value means that the concentration was not tested)

| Structure | effect on methanogenesis (%) | | | | | | |
|---|---|---|---|---|---|---|---|
| | 2% DM | 1% DM | 0.5% DM | 0.25% DM | 0.1% DM | 0.05% DM | 0.01% DM |
| $O_2N{-}O{-}CH_2CH_2{-}C(O){-}O{-}CH_3$ | −100 | −100 | | | | −64 | −12 |
| $O_2N{-}O{-}CH_2CH_2{-}C(O){-}OH$ | −100 | −100 | | | −100 | −98 | −8 |
| $O_2N{-}O{-}CH(CH_3){-}C(O){-}O{-}Et$ | −100 | −33 | | | −2 | | |
| $O_2N{-}O{-}(CH_2)_3{-}C(O){-}O{-}Et$ | −100 | −100 | | | −82 | −55 | −6 |
| $O_2N{-}O{-}(CH_2)_3{-}C(O){-}OH$ | 2 | | | | | | |
| $O_2N{-}O{-}CH(CH_3){-}CH_2{-}C(O){-}O{-}Et$ | −100 | −100 | | | −17 | | |
| $O_2N{-}O{-}(CH_2)_4{-}C(O){-}O{-}Et$ | −100 | −100 | | | | −87 | −28 |
| $O_2N{-}O{-}(CH_2)_4{-}C(O){-}OH$ | −100 | −100 | | | −100 | −100 | −23 |
| HOOC{-}C(CH_3)_2{-}CH_2{-}O{-}NO_2 | −100 | −49 | | | | | |
| $O_2N{-}O{-}(CH_2)_5{-}C(O){-}O{-}Et$ | | | | | −100 | −78 | −3 |
| $O_2N{-}O{-}(CH_2)_5{-}C(O){-}OH$ | | | | | −100 | −99 | −10 |
| $O_2N{-}O{-}(CH_2)_6{-}C(O){-}O{-}Et$ | | | | | −99 | −96 | −12 |

TABLE 2-continued

Methane reduction effect resulting from the average of two experiments with some compounds according to the present invention (a minus sign followed by an integer in the column effect on methanogenesis (%) means a reduction in methane produced when compared to control; no value means that the concentration was not tested)

| Structure | effect on methanogenesis (%) | | | | | | |
|---|---|---|---|---|---|---|---|
| | 2% DM | 1% DM | 0.5% DM | 0.25% DM | 0.1% DM | 0.05% DM | 0.01% DM |
| 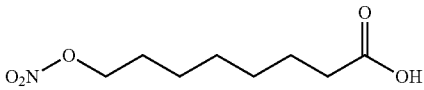 | | | | | −100 | −76 | −7 |
| 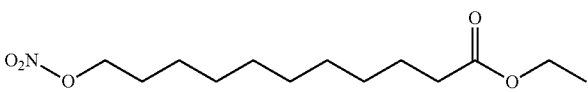 [SMILES: CCOC(=O)CCCCCCCCCCO[N+](=O)[O-]] | | | | | −99 | −48 | −8 |
| 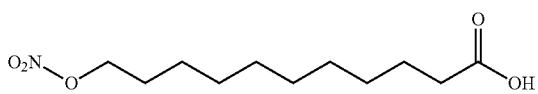 [SMILES: O=C(O)CCCCCCCCCCO[N+](=O)[O-]] | | | | | −99 | −52 | −13 |
| 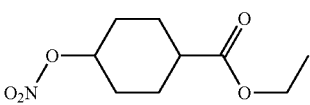 | | | −98 | | −88 | −2 | |
| 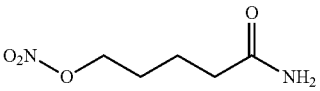 [SMILES: NC(=O)CCCCO[N+](=O)[O-]] | | | −98 | | −99 | −2 | |
| 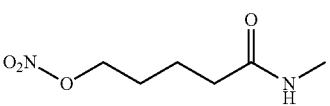 | | | −98 | | −100 | −2 | |
| Na NO3 | | | −23 | −2 | | | |

Example 2

In Vivo Test for Methane Inhibition

1. Material and Methods

The experimental design consisted of a cross-over design with 2 sheep per treatment in each period. The trial consisted in 3 consecutive periods of: 14 days of adaptation to the dose plus three consecutive days of methane measurements in chambers. This 14 days adaptation phase was established as the period necessary for wash out between different doses assayed in consecutive periods. During the last two days of methane measurements in chambers rumen contents samples were collected two hours after the morning feeding, sub sampled and immediately frozen prior DNA extraction and determination of volatile fatty acids and ammonia nitrogen concentration. Experimental animals were randomly allocated in three sub-groups of 2 animals and were assigned one of the three treatments (control, dose 1 and dose 2). The 3 sub-groups started the adaptation period with a gap of three days so they had the same number of adaptation days prior to methane measurement in the chambers. Each animal was held in cages with constant access to fresh water. The diet provided to the animals consisted of alfalfa hay chopped at 15 to 20 cm and concentrate in a proportion 1:1 at approximately 1.1 times the energy requirements maintenance level (Prieto et al, 1990) plus mineral-vitamin supplement. Fresh matter intake was monitored daily for each animal throughout the trial. The diet was provided to animals in two equal meals at 9.00 h and 14.00 h.

The additive was provided twice a day through the ruminal cannula at the same time as the diet. The corresponding amount to each dose was added into 10 grams of grounded concentrate and wrapped in cellulose paper immediately before it was placed in the rumen. In order to avoid the volatility of the active molecule, both additives were kept in a cold room at 4° C. where the daily process of dispensing it in the cellulose bags was carried out.

The doses were 50 (dose 1) and 500 (dose 2) mg/animal per day. The higher dose was reached after 3 days of gradual increases (50, 200 and 500 mg), so the whole adaptation period was consequently extended for 3 more days.

The additive tested in this experiment was Ethyl-3-nitrooxy propionate of the following formula:

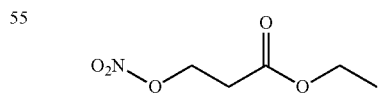

Methane Measurement

On day 14 animals were introduced in the chambers for methane measurements for 3 consecutive days. Each chamber measured 1.8 m wide×1.8 m deep×1.5 m tall. Chamber air temperature was maintained between 15 and 20° C. Within each chamber, the animals were individually restrained in the same cages as in the adaptation period. Interruptions occurred daily at 8.30 h, when the chamber floor was cleaned, and the animals were fed. These interruptions had little impact on the daily emissions because fluxes were calculated three times per day and then averaged to derive the 23-hour emission value. Airflow and concentration of methane was measured for the intake and exhaust ducts of each chamber. Air velocity was continuously monitored over the day in each intake and exhaust duct for each chamber. The air stream in each of the 3 ducts (chamber 1, chamber 2 and background) was sub-sampled, and methane concentration was measured continuously using a gas analyzer ADM MGA3000 (Spurling works, Herts, UK). It took 8 min. to sequentially sample the airflow in all intake and exhaust ducts in both chambers (3 min. in chambers 1 and 2, 2 min for background). In summary, the flux of methane for each chamber was calculated for each of the 3-day periods of measurement from the difference of fresh-air input and chamber exhaust methane concentrations and mean air velocities.

Rumen Samples Analysis

Samples of rumen contents were freeze-dried and thoroughly mixed by physical disruption using a bead beater (Mini-bead Beater; BioSpec Products, Bartlesville, Okla., USA) before DNA extraction, which was performed from approximately 50 mg sample using the QIAamp® DNA Stool Mini Kit (Qiagen Ltd, West Sussex, UK) following the manufacturer's instructions with the modification that a higher temperature (95° C.) was used for lysis incubation. DNA samples were used as templates for quantitative real-time PCR (qPCR) amplification. The numbers of total bacteria, total protozoa and total methanogenic archaea were quantified by Real Time—PCR (qPCR).

Different primer sets were used to amplify 16S rRNA gene-targeted total bacteria (Maeda et al. *FEMS Inmunology and Medical Microbiology* 39, 81-86, 2003), and protozoa (Sylvester et al. *Journal Dairy Science*. 88, 2083-2095 2005). Primers designed for the detection of methanogenic archaea were targeted against the methyl coenzyme-M reductase (mcrA) gene (Denman et al. *FEMS Microbiology Ecology*. 62, 313-322, 2007). The amplifications mixture contained 11.5 μl 2×RT-PCR supermix BioRad (Bio-Rad Laboratories Inc., Hercules, Calif., USA), 0.4 μl of each primer (50 pmol) and 0.5 μl of sample in a final volume of 23 μl. The amplification efficiency was evaluated for each pair of primers with the following program: 5 min cycle at 95° C., 40 cycles at 95° C. for 15 s, 60° C. for 30 s, 72° C. for 55 s and, 75° C. during 6 s for fluorescent emission measures. The melting curve was built by increasing temperature from 55° C. to 95° C. and reading were taken every 5° C. Amplification of each target group was carried out with the following program: 5 min cycle at 95° C., 40 cycles at 95° C. for 15 s, 15 s at 60° C. and 72° C. for 45 s (including the fluorescence emission measuring) and a melting curve with a set point temperature of 45° C. and end temperature of 95° C. The absolute amount of bacteria, protozoa and methanogenic archaea expressed as the number of DNA copies, was determined by using standards. The qPCR standards consisted of the plasmid pCR®4-TOPO (Invitrogen™, Carlsbad, Calif., USA). The PCR product obtained using the respective set of primers was purified and then cloned into PCR® 4-TOPO® plasmid (Invitrogen™, Carlsbad, Calif., USA) to produce recombinant plasmids. A single colony, verified for the expected insert using PCR, was grown in solid media with antibiotics and X-gal overnight. Afterwards, a screening of transformed *E. coli* colonies was done and some of the positive ones were randomly selected. After checking the presence of the inserted fragment in the colonies by PCR, massive culture of positive colonies was done in liquid media overnight. Plasmids belonging to these cultures were extracted using the Pure Link™ Miniprep kit (Invitrogen™, Carlsbad, Calif., USA) and then sequenced to verify the presence of the fragment inserted. The number of 16S rRNA gene copies present in the plasmid extracts was calculated using the plasmid DNA concentration and the molecular mass of the vector with the insert. The concentrated plasmid was serially diluted (10-fold) to provide a range of $10^8$ to $10^2$ copies. Serially diluted samples were used to generate a standard curve.

Volatile fatty acids were analysed by gas chromatography and ammonia N concentration by colorimetry according to (Cantalapiedra-Híjar et al. *Journal of Animal Science*. 87, 622-631, 2009).

Statistical Analysis

Individual methane emissions, VFA profiles, ratio of acetate to propionate, ammonia N concentration, and $\log_{10}$ transformations of concentration of total bacteria, total protozoa and methanogenic archaea were analyzed for the following effects: additive dose, day of measurement, and their interaction using a repeated measures analysis of variance under the cross-over design arrangement of the experiment. The standard error of the mean (SEM) was computed for each analysis. No significant effect of the measuring day or its interaction with additive dose was detected in either experiments, so only the effect of the dose is included in the tables. Means were further compared using a least significant difference (LSD) procedure. The SPSS for Windows, version 14.0 (2005; SPSS Inc., Chicago, Ill.) was used for data entry and statistical analysis.

2. Results

Fresh matter intake did not change along the adaptation period for animals in trial. Likewise, the body weight (as an average of weighing prior and after chamber measurements) was not different among treatments (Table 3). Methane emissions either net or per unit of weight/intake, was significantly reduced when Ethyl-3-nitrooxy propionate additive was incorporated in the diet, although the statistical difference was only reached when the high dose was used (P<0.05). The reduction observed was 18% and 29%, respectively for doses 1 and 2 and seemed to happen in the first days of the adaptation as intermediate values obtained 7 days after each period began showed the same trend described above.

TABLE 3

Effect of the addition of Ethyl-3-nitrooxy propionate additive on body weight, feed intake and methane emissions by sheep (average of 3 consecutive days measurement). Adaptation = data recorded half way through the adaptation period.

|  | Control n = 5 | Dose 1 n = 5 | Dose 2 n = 5 | SEM | P value |
|---|---|---|---|---|---|
| Body weight, kg* | 43.2 | 43.9 | 42.6 | 49.7 | 0.729 |
| DMI, g/day | 809.5 | 858.5 | 809.7 | 1.955 | 0.019 |
| CH4, l/day | $25.5^a$ | $22.3^{ab}$ | $18^b$ | 1.955 | 0.019 |
| CH4, l/kg BW | $0.59^a$ | $0.51^{ab}$ | $0.42^b$ | 0.050 | 0.037 |
| CH4, l/kg DMI | $31.5^a$ | $26.0^{ab}$ | $22.2^b$ | 2.59 | 0.029 |

$^{a,b}$Values in a row not sharing a common superscript letters significantly differ, P < 005.
*Average of weights recorded prior and after chamber measurements.

The study of the rumen fermentation parameters showed a shift in the fermentation pathways (Table 4) towards a more propionic type profile in the rumen of animals receiving the additive, especially those treated with the higher dose. This was reflected in a decrease in the acetate to propionate ratio (P<0.05) as the dose of the additive increased. The concentration of ammonia N was similar among treatments.

TABLE 4

Effect of the addition of Ethyl-3-nitrooxy propionate additive on volatile fatty acid concentration (mmol/l) and profile (mol/100 mol) and ammonia Nitrogen concentration (mg/100 ml) in the rumen of sheep.

| | Control n = 5 | Dose 1 n = 5 | Dose 2 n = 5 | SEM | P value |
|---|---|---|---|---|---|
| Acetic | 70.6[a] | 71.0[a] | 65.5[b] | 0.890 | 0.001 |
| Propionic | 15.7[a] | 16.8[ab] | 18.8[b] | 0.897 | 0.029 |
| Butiric | 3.69 | 3.50 | 3.47 | 0.195 | 0.696 |
| iso-butiric | 6.73[ab] | 5.57[a] | 8.06[b] | 0.570 | 0.010 |
| Valeric | 1.69[a] | 1.55[a] | 2.42[b] | 0.189 | 0.007 |
| iso-valeric | 1.60 | 1.50 | 1.76 | 0.105 | 0.247 |
| C2/C3 | 4.59[a] | 4.26[ab] | 3.57[b] | 0.230 | 0.008 |
| Total (mmol/l) | 111.3[ab] | 123.3[a] | 104.1[b] | 5.527 | 0.030 |
| $NH_3$—N | 42.5 | 40.5 | 40.1 | 5.847 | 0.953 |

[a,b]Values in a row not sharing a common superscript letters significantly differ, P < 005.

The study of the concentration of the main microbial groups in the rumen showed no difference among treatments. However, for total bacteria and methanogenic archaea respectively a numerical increase and decrease was observed as the animals received a higher dose of the additive.

TABLE 5

Effect of the addition of Ethyl-3-nitrooxy propionate on the concentration (copy gene numbers/g fresh matter) of total bacteria (16SrRNA), protozoa (18SrRNA) and methanogenic archaea (mcrA gene) in the rumen of sheep.

| | Control n = 5 | Dose 1 n = 5 | Dose 2 n = 5 | SEM | P value |
|---|---|---|---|---|---|
| Total bacteria | $1.19 \times 10^9$ | $1.43 \times 10^9$ | $1.63 \times 10^9$ | | |
| $\log_{10}$ | 9.03 | 9.08 | 9.18 | 0.105 | 0.591 |
| Total protozoa | $2.38 \times 10^6$ | $2.08 \times 10^6$ | $2.77 \times 10^6$ | | |
| $\log_{10}$ | 6.35 | 6.28 | 6.43 | 0.063 | 0.277 |
| Methanogenic archaea | $5.60 \times 10^3$ | $5.43 \times 10^3$ | $4.34 \times 10^3$ | | |
| $\log_{10}$ | 3.59 | 3.57 | 3.45 | 0.225 | 0.933 |

3. Conclusions

Ethyl-3-nitrooxy propionate appears as a strong inhibitor of methanogenesis, provoking a shift in the metabolic pathways involved in $H_2$ transferring.

Example 3

Synthesis of Ethyl 3-nitro-oxy-propionate

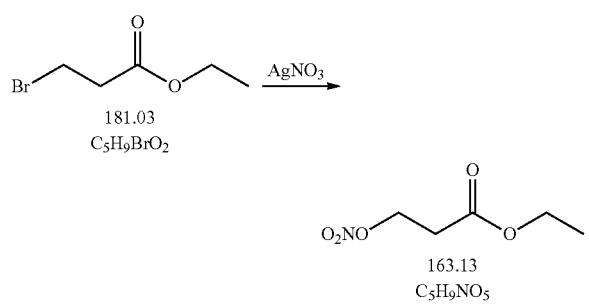

30 mmol ethyl 3-bromopropionate dissolved in 150 ml acetonitrile and 75 mmol silver nitrite were added into a flask protected from light. This suspension was stirred for 5 hours at 70° C. After cooling to room temperature the suspension was filtrated and concentrated in vacuo. The residue was dissolved in dichloromethane and extracted with water. The water phase was washed again with dichloromethane. The combined organic phase was washed with water and brine, dried over $Na_2SO_4$ and the solvent was removed in vacuo leaving 4.88 g (29.9 mmol, 99.7%).

Example 4

Synthesis of 3-Nitro-oxy-propionic acid

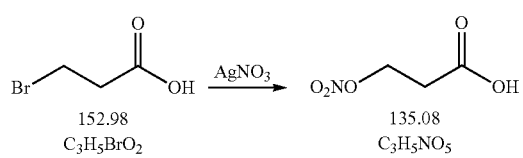

14.6 mmol 3-bromopropionic acid dissolved in 120 ml acetonitrile and 36.5 mmol silver nitrite were added into a flask protected from light. This suspension was stirred for 7 hours at 70° C. After cooling to room temperature the suspension was filtrated and concentrated in vacuo. The residue was dissolved in dichloromethane and extracted with water. The water phase was washed again with dichloromethane. The combined organic phase was washed with water and brine, dried over $Na_2SO_4$ and the solvent was removed in vacuo leaving 1.17 g.

The crude product was purified by flash chromatography on silica gel using hexane/ethyl acetate 4:1; Yield: 0.51 g (3.77 mmol, 25.8%).

Example 5

Synthesis of Ethyl 4-nitro-oxy-butanoate

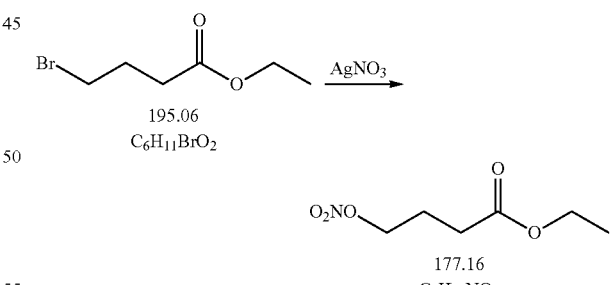

14.6 mmol ethyl 4-bromobutanonate dissolved in 120 ml acetonitrile and 36.5 mmol silver nitrite were added into a flask protected from light. This suspension was stirred for 7 hours at 70° C. After cooling to room temperature the suspension was filtrated and concentrated in vacuo. The residue was dissolved in dichloromethane and extracted with water. The water phase was washed again with dichloromethane. The combined organic phase was washed with water and brine, dried over $Na_2SO_4$ and the solvent was removed in vacuo leaving 2.63 g.

The crude product was purified by flash chromatography on silica gel using hexane/ethyl acetate 4:1; Yield: 1.9 g (10.7 mmol, 73.5%).

Example 6

Synthesis of 4-Nitro-oxy-butanoic acid

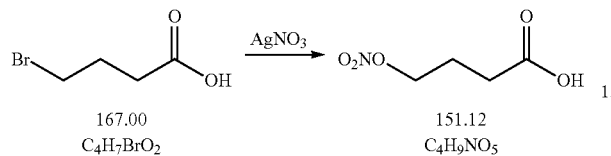

14.1 mmol 4-bromobutanoic acid dissolved in 115 ml acetonitrile and 35.1 mmol silver nitrite were added into a flask protected from light. This suspension was stirred for 6 hours at 70° C. After cooling to room temperature the suspension was filtrated and concentrated in vacuo. The residue was dissolved in dichloromethane and extracted with water. The water phase was washed again with dichloromethane. The combined organic phase was washed with water and brine, dried over $Na_2SO_4$ and the solvent was removed in vacuo leaving 1.04 g.

The crude product was purified by flash chromatography on silica gel using hexane/ethyl acetate 4:1; Yield: 0.54 g (3.6 mmol, 25.4%).

Example 7

Synthesis of Ethyl 5-nitro-oxy-pentanoate

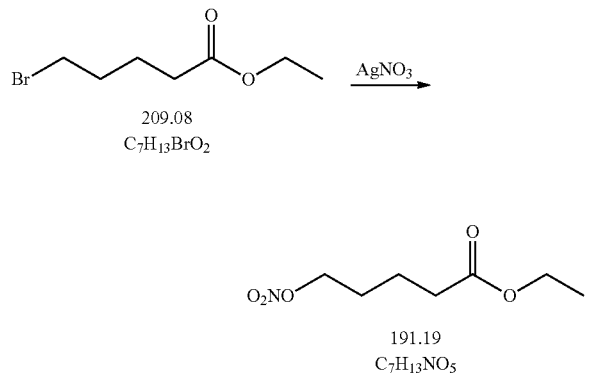

14.1 mmol ethyl 5-bromovalerate dissolved in 115 ml acetonitrile and 35.1 mmol silver nitrite were added into a flask protected from light. This suspension was stirred for 6 hours at 70° C. After cooling to room temperature the suspension was filtrated and concentrated in vacuo. The residue was dissolved in dichloromethane and extracted with water. The water phase was washed again with dichloromethane. The combined organic phase was washed with water and brine, dried over $Na_2SO_4$ and the solvent was removed in vacuo leaving 2.66 g.

The crude product was purified by flash chromatography on silica gel using hexane/ethyl acetate 4:1; Yield: 2.23 g (11.7 mmol, 83%).

Example 8

Synthesis of 5-Nitro-oxy-vpentanoic acid

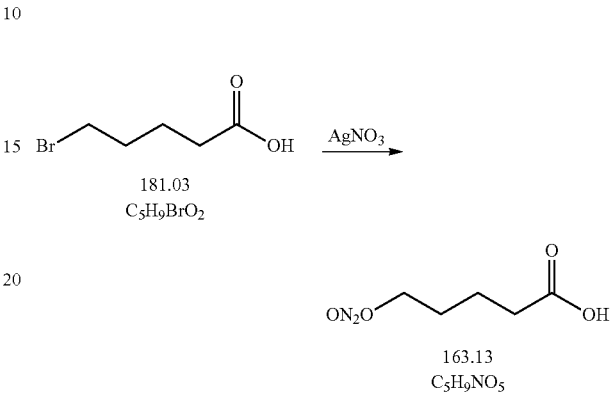

78.7 mmol 5-bromovaleric acid 200 ml acetonitrile and 196.75 mmol silver nitrite were added into a flask protected from light. This suspension was stirred for 4 hours and 30 min at 70° C. After cooling to room temperature the suspension was filtrated and concentrated in vacuo. The residue was dissolved in Water and extracted two times with TMBE. The organic phases were washed with water and brine, combined, dried over $Na_2SO_4$ and the solvent was removed in vacuo leaving 7.54 g.

The crude product was purified by flash chromatography on silica gel using heptane/ethyl acetate 1:1; Yield: 7.19 g (44.1 mmol, 56.0%).

Example 9

Synthesis of Ethyl 2-nitro-oxy-propionate

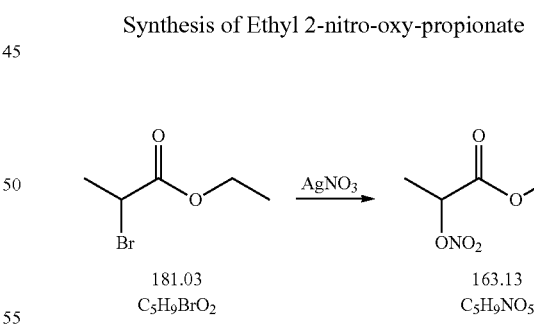

14.1 mmol ethyl 2-bromopropionate dissolved in 115 ml acetonitrile and 36.1 mmol silver nitrite were added into a flask protected from light. This suspension was stirred for 6 hours at 70° C. After cooling to room temperature the suspension was filtrated and concentrated in vacuo. The residue was dissolved in dichloromethane and extracted with Water. The water phase was washed again with dichloromethane. The combined organic phase was washed with water and brine, dried over $Na_2SO_4$ and the solvent was removed in vacuo leaving 2.02 g (12.4 mmol, 88.1%).

Example 10

Synthesis of Ethyl 6-nitrooxy-hexanoate

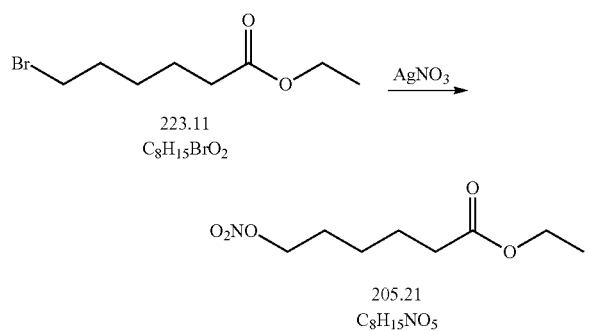

48.80 mmol Ethyl 6-bromohexanoate dissolved in 100 ml acetonitrile and 122.0 mmol silver nitrite were added into a flask protected from light. This suspension was stirred for 19 hours at 70° C. After cooling to room temperature the suspension was filtrated and concentrated in vacuo. The residue was dissolved in dichloromethane and extracted with Water. The water phase was washed again with dichloromethane. The combined organic phase was washed with water and brine, dried over $Na_2SO_4$ and the solvent was removed in vacuo leaving 10.06 g.

The crude product was purified by flash chromatography on silica gel using hexane/ethyl acetate 4:1; Yield: 9.72 g (47.4 mmol, 97.1%).

Example 11

Synthesis of 6-Nitrooxy-hexanoic acid

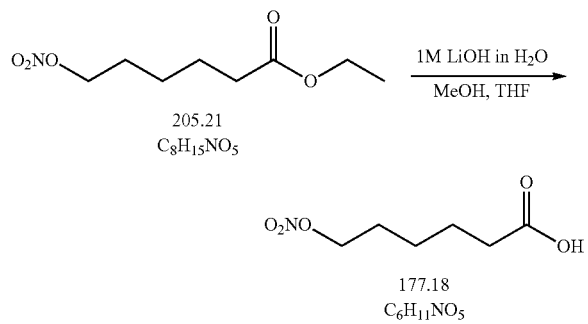

19.1 mmol Ethyl 6-nitrooxy-hexanoate were dissolved in 222 ml Methanol/THF 1:1. 37.5 ml 1M Lithiumhydroxide in Water were added to the reaction and the cloudy solution was heated for 18 hours at 50° C. After cooling to room temperature the solution was concentrated in vacuo. The pH level of the solution was brought down to 1 with HCl 25% and extracted two times with TMBE. The organic phases were combined, washed with brine, dried over $Na_2SO_4$ and the solvent was removed in vacuo leaving 3.43 g.

The crude product was purified by flash chromatography on silica gel using hexane/ethyl acetate 1:1; Yield: 2.96 g (16.7 mmol, 87.5%).

Example 12

Synthesis of Methyl 3-Nitro-oxy-propionate

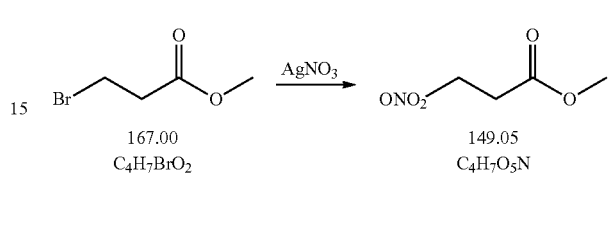

10 mmol Methyl 3-bromopropionate dissolved in 40 ml acetonitrile and 25 mmol silver nitrite were added into a flask protected from light. This suspension was stirred for 5 hours at 70° C. After cooling to room temperature the suspension was filtrated and concentrated in vacuo. The residue was dissolved in dichloromethane and extracted with Water. The water phase was washed again with two times with dichloromethane. The combined organic phase was washed with water and brine, dried over $Na_2SO_4$ and the solvent was removed in vacuo leaving 1.39 g.

The crude product was purified by flash chromatography on silica gel using hexane/ethyl acetate 5:1; Yield: 0.43 g (2.9 mmol, 28%).

Example 13

Synthesis of Ethyl 3-nitro-oxy-butanoate

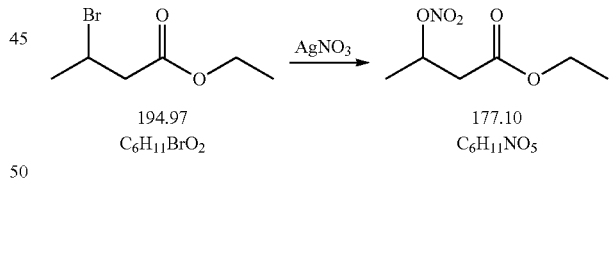

14.1 mmol ethyl 3-bromobutanoate dissolved in 80 ml acetonitrile and 35.1 mmol silver nitrite were added into a flask protected from light. This suspension was stirred for 5 hours at 70° C. After cooling to room temperature the suspension was filtrated and concentrated in vacuo. The residue was dissolved in dichloromethane and extracted with Water. The water phase was washed again with two times with dichloromethane. The combined organic phase was washed with water and brine, dried over $Na_2SO_4$ and the solvent was removed in vacuo leaving 2.03 g.

The crude product was purified by flash chromatography on silica gel using hexane/ethyl acetate 5:1; Yield: 1.35 g (7.6 mmol, 53.3%).

Example 14

Synthesis of 8-Nitrooxy-octanoic acid

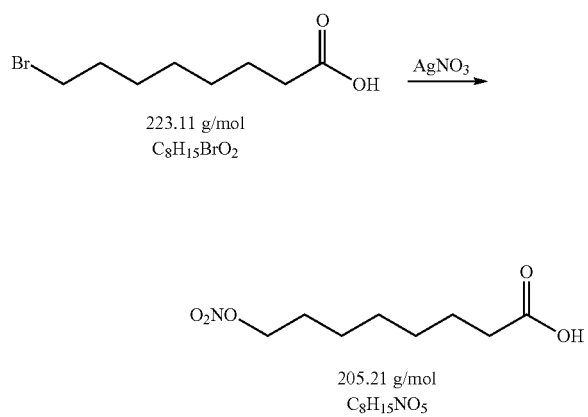

21.75 mmol 8-bromooctanoic acid dissolved in 60 ml acetonitrile and 54.4 mmol silver nitrite were added into a flask protected from light. This suspension was stirred for 20 hours and 30 min at 70° C. After cooling to room temperature the suspension was filtrated and concentrated in vacuo. The residue was dissolved in Water and extracted with TMBE. The organic phases were washed with water and brine, combined, dried over $Na_2SO_4$ and the solvent was removed in vacuo leaving 4.44 g.

The crude product was purified by flash chromatography on silica gel using heptane/ethyl acetate 1:1; Yield: 3.99 g (19.4 mmol, 89.4%).

Example 15

Synthesis of Ethyl 8-nitrooxy-octanoate

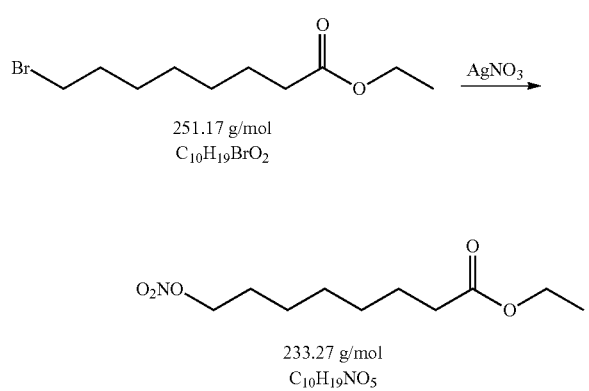

20.0 mmol Ethyl 8-bromooctanoate dissolved in 80 ml acetonitrile and 50.0 mmol silver nitrite were added into a flask protected from light. This suspension was stirred for 18 hours at 70° C. After cooling to room temperature the suspension was filtrated over silica gel, washed with Ethylacetate and concentrated in vacuo.

The crude product was purified by flash chromatography on silica gel using heptane/ethyl acetate 4:1; Yield: 4.35 g (18.6 mmol, 93.2%).

Example 16

Synthesis of Ethyl 11-nitrooxy-undecanoate

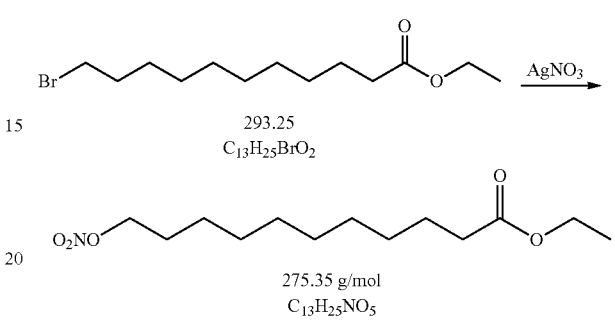

13.8 mmol Ethyl 11-bromoundecanoate dissolved in 60 ml acetonitrile and 34.6 mmol silver nitrite were added into a flask protected from light. This suspension was stirred for 19.5 hours at 60° C. After cooling to room temperature the suspension was and concentrated in vacuo. The residue was dissolved in dichloromethane and extracted with Water. The water phase was washed again with dichloromethane. The combined organic phase was washed with water and brine, dried over $Na_2SO_4$ and the solvent was removed in vacuo leaving 4.86 g.

The crude product was purified by flash chromatography on silica gel using heptane/ethyl acetate 20:1; Yield: 3.6 g (13.1 mmol, 95.0%).

Example 17

Synthesis of 11-Nitrooxy-undecanoic acid

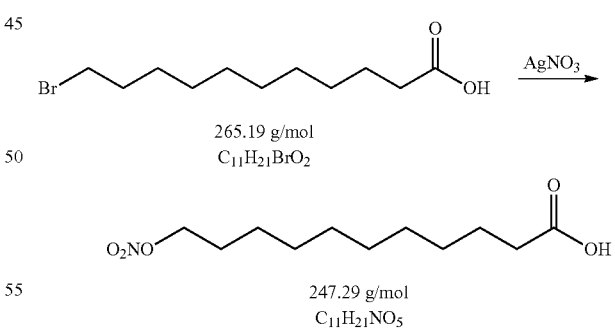

18.7 mmol 11-bromoundecanoic acid dissolved in 60 ml acetonitrile and 46.6 mmol silver nitrite were added into a flask protected from light. This suspension was stirred for 21 hours and 30 min at 70° C. After cooling to room temperature the suspension was filtrated and concentrated in vacuo. The residue was dissolved in Water and extracted with TMBE. The organic phases were washed with water and brine, combined, dried over $Na_2SO_4$ and the solvent was removed in vacuo leaving 4.34 g.

The crude product was purified by flash chromatography on silica gel using heptane/ethyl acetate 2:1; Yield: 4.01 g (16.1 mmol, 86.2%).

Example 18

Synthesis of 5-Nitrooxy-pentanoic acid methylamide

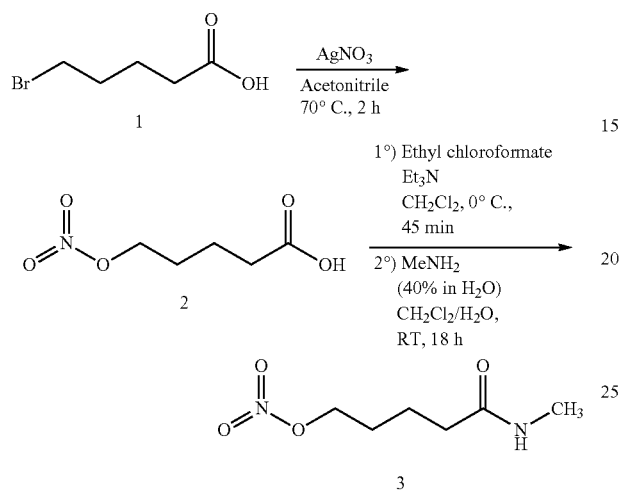

Synthesis of 5-Nitrooxy-pentanoic acid 2

To a solution of 5-bromovaleric acid 1 (5.00 g, 1.0 eq) in 50.0 mL of dry acetonitrile was added silver nitrate (5.10 g, 1.1 eq). The reaction mixture was heated in the dark at 70° C. for 2 hours. The resulting mixture was filtered off through celite and the filtrate was concentrated under vacuum. The residue was dissolved into an aqueous solution of hydrochloric acid (1N) (100.0 mL), extracted with dichloromethane (2×100.0 mL), dried over magnesium sulphate and solvents were evaporated under vacuum to afford compound 2 as a colourless liquid. (2.92 g, yield=65%).

Synthesis of 5-Nitrooxy-pentanoic acid methylamide 3

To a solution of compound 2 (1.60 g, 1.0 eq) in dry dichloromethane (20.0 mL) cooled to 0° C. was added triethylamine (1.70 mL, 1.2 eq) followed by ethyl chloroformate (1.10 mL, 1.1 eq). The reaction mixture was stirred at 0° C. for 45 minutes and 40% aqueous methyl amine (20.0 mL) was added. The solution was stirred from 0° C. to RT for 18 hours and sodium sulphate was added to dry the reaction mixture. The resulting mixture was filtered off and the filtrate was concentrated under vacuum. The residue was adsorbed on silica gel and purified by flash chromatography [Biotage®, dichloromethane/methanol 100/0→97/3 (15CV*)] affording compound 3 as a colourless liquid (0.84 g, yield=47%).

The final compound was dried at 60° C. under reduced pressure for 18 hours. Degradation was observed by $^1$H NMR. The degraded compound was adsorbed on silica gel and purified by flash chromatography [Biotage®, dichloromethane/methanol 100/0→98/2 (15CV), 98/2 (4CV)] affording compound 3 as a light yellow liquid (0.59 g, yield=33%).

No further degradation was observed after 1 week at room temperature.

*CV=Column Volume

Example 19

Synthesis of 4-Nitrooxy-cyclohexylcarboxylic acid ethyl ester

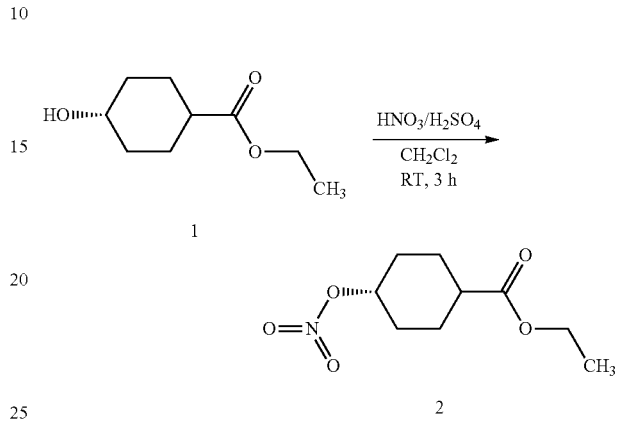

Concentrated sulphuric acid 96% (1.24 mL, 2.0 eq) was added dropwise to fuming nitric acid 100% (0.97 mL, 2.0 eq) at 0° C. After 10 minutes of stirring at 0° C., a solution of 1 (2.00 g, 1.0 eq) in dichloromethane (20.0 mL) was added dropwise. The reaction mixture was stirred from 0° C. to RT for 3 hours and quenched with water (30.0 mL). The organic layer was washed with water (20.0 mL) and brine (20.0 mL), dried over magnesium sulphate, filtered off and concentrated under vacuum. The residue was adsorbed on silica gel and purified by flash chromatography [Biotage®, dichloromethane/methanol 100/0→97/3 (10CV*), 97/3 (5CV)] affording compound 2 as a colourless liquid (1.47 g, yield=58%).

Example 20

Synthesis of 5-Nitrooxy-pentanoic acid amide

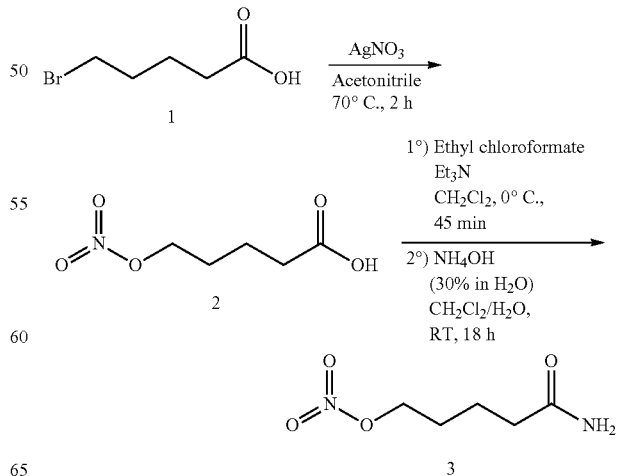

Synthesis of 5-Nitrooxy-pentanoic acid 2

To a solution of 5-bromovaleric acid 1 (5.00 g, 1.0 eq) in 50.0 mL of dry acetonitrile was added silver nitrate (5.10 g, 1.1 eq). The reaction mixture was heated in the dark at 70° C. for 2 hours. The resulting mixture was filtered off through celite and the filtrate was concentrated under vacuum. The residue was dissolved into an aqueous solution of hydrochloric acid (1N) (100.0 mL), extracted with dichloromethane (2×100.0 mL), dried over magnesium sulphate and solvents were evaporated under vacuum to afford compound 2 as a colourless liquid. (2.92 g, yield=65%).

Synthesis of 5-Nitrooxy-pentanoic acid amide 3

To a solution of compound 2 (1.30 g, 1.0 eq) in dry dichloromethane (20.0 mL) cooled to 0° C. was added triethylamine (1.30 mL, 1.2 eq) followed by ethyl chloroformate (0.83 mL, 1.1 eq). The reaction mixture was stirred at 0° C. for 45 minutes and 30% aqueous ammonia solution (15.0 mL) was added. The solution was stirred from 0° C. to RT for 18 hours and sodium sulphate was added to dry the mixture. The resulting mixture was filtered off and the filtrate was concentrated under vacuum. The residue was adsorbed on silica gel and purified by flash chromatography [Biotage®, dichloromethane/methanol 100/0→98/2 (12CV*), 98/2 (6CV)] affording compound 3 as a white solid (1.10 g, yield=85%).

The final compound was dried at 60° C. under reduced pressure for 18 hours. Degradation was observed by $^1$H NMR. The degraded compound was adsorbed on silica gel and purified by flash chromatography [Biotage®, dichloromethane/methanol 100/0→98/2 (12CV), 98/2 (6CV)] affording compound 3 as a white solid (0.90 g, yield=70%).

No further degradation was observed after 1 week at room temperature.

The invention claimed is:

1. A feed composition or feed additive comprising at least one nitrooxy alkanoic acid and derivative thereof as defined by formula (I);

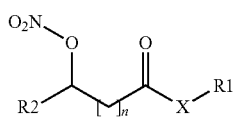

as an active compound in the animal feed composition or feed additive for reducing the formation of methane emanating from the digestive activities of ruminants, and/or for improving ruminant performance, wherein n is a number between 0 and 23 and, wherein if n≠0, then the carbon chain is a linear, a cyclic, or branched linear or cyclic aliphatic carbon chain which may be mono- or polyunsaturated and in any isomeric form, X is independently O, NH, or N—R3, wherein if R1≠H, then X—R1-represents an ester or a secondary amide derivative, R1 is independently, hydrogen or a saturated straight, cyclic or branched chain of an alkyl or alkenyl group containing 1 to 10 carbon atoms, R2 is independently, hydrogen or a saturated straight or branched chain of an alkyl or alkenyl group containing 1 to 23 carbon atoms, and R3 is independently, hydrogen or a saturated straight, cyclic or branched chain of an alkyl or alkenyl group containing 1 to 10 carbon atoms, and wherein the feed composition or feed additive is a mineral premix, a vitamin premix, or a premix including vitamins and minerals.

2. The feed composition or feed additive of claim 1, wherein n is a number between 0 and 9, and wherein, if n≠0, then the carbon chain is a linear, a cyclic, or branched linear or cyclic aliphatic carbon chain in any isomeric form, X is independently O, NH, or N—R3, wherein if R1≠H, then X—R1-represents an ester or a secondary amide derivative, R1 is independently, hydrogen or a saturated straight or branched chain of an alkyl or alkenyl group containing 1 to 5 carbon atoms, R2 is independently, hydrogen or a saturated straight or branched chain of an alkyl or alkenyl group containing 1 to 9 carbon atoms, and R3 is independently, hydrogen or a saturated straight or branched chain of an alkyl or alkenyl group containing 1 to 5 carbon atoms.

3. The feed composition or feed additive of claim 1, wherein

R1 is selected from the group consisting of hydrogen (H), methyl, and ethyl,

R2 is independently selected from the group consisting of hydrogen (H), methyl, and ethyl, R3 is independently selected from the group consisting of hydrogen (H), methyl, and ethyl.

4. The feed composition or feed additive of claim 1, wherein

R1 is selected from the group consisting of hydrogen (H), methyl, and ethyl,

R2 is a hydrogen (H),

R3 is independently selected from the group consisting of hydrogen (H), methyl, and ethyl.

5. The feed composition or feed additive of claim 1, wherein

X is oxygen (O), wherein if R1≠H, then X—R1- represents an ester, and

R2 is a hydrogen (H).

6. A feed composition or feed additive comprising at least one nitrooxy alkanoic acid and/or derivative thereof which is selected from the group consisting of 3-nitrooxy propionic acid, methyl-3-nitrooxy propionate, ethyl-3-nitrooxy propionate, ethyl-4-nitrooxy-butanoate, ethyl-3-nitrooxy-butanoate, 5-nitrooxy pentanoic acid, ethyl-5-nitrooxy pentanoate, 6-nitrooxy hexanoic acid, ethyl-6-nitrooxy hexanoate, ethyl-4-nitrooxy-cyclohexylcarboxylate, 8-nitrooxy octanoic acid, ethyl-8-nitrooxy octanoate, 11-nitrooxy undecanoic acid, ethyl-11-nitrooxy undecanoate, 5-nitrooxy-N-pentanoic amide, and 5-nitrooxy-N-methyl-pentanoic amide.

7. The feed composition or feed additive of claim 6, which further comprises at least one additional active substance selected from the group consisting of diallyl disulfide, garlic oil, allyl isothiocyanate, deoxycholic acid, chenodeoxycholic acid and derivatives thereof.

8. The feed composition or feed additive of claim 1, wherein the ruminant animal is selected from the group consisting of: cattle, goats, sheep, giraffes, American Bison, European bison, yaks, water buffalo, deer, camels, alpacas, llamas, wildebeest, antelope, pronghorn, and nilgai.

9. The feed composition or feed additive of claim 1, wherein the at least one active compound is present in an amount sufficient to reduce methane production in ruminants calculated in liters per kilogram of dry matter intake by at least 10% when measured in metabolic chambers.

10. The feed composition or feed additive of claim 1, wherein the at least one active compound is present in an amount from 1 mg to 10 g per kg feed.

11. The feed composition or feed additive of claim 1, wherein R1 is a saturated straight, cyclic or branched chain of an alkyl or alkenyl group containing 1 to 5 carbon atoms.

12. The feed composition or feed additive of claim 1, wherein R2 is a saturated straight, cyclic or branched chain of an alkyl or alkenyl group group containing 1 to 9 carbon atoms.

13. The feed composition or feed additive of claim 1, wherein R3 is a saturated straight, cyclic or branched chain of an alkyl or alkenyl group group containing 1 to 5 carbon atoms.

14. A feed composition or feed additive comprising at least one nitrooxy alkanoic acid and derivative thereof as defined by formula (I):

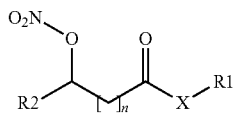

(I)

as an active compound in the animal feed composition or feed additive for reducing the formation of methane emanating from the digestive activities of ruminants, and/or for improving ruminant performance, wherein n is a number between 0 and 23 and, wherein if n≠0, then the carbon chain is a linear, a cyclic, or branched linear or cyclic aliphatic carbon chain which may be mono- or polyunsaturated and in any isomeric form, X is independently O, NH, or N—R3, wherein if R1≠H, then X—R1-represents an ester or a secondary amide derivative, R1 is independently, hydrogen or a saturated straight, cyclic or branched chain of an alkyl or alkenyl group containing 1 to 10 carbon atoms, R2 is independently, hydrogen or a saturated straight or branched chain of an alkyl or alkenyl group containing 1 to 23 carbon atoms, and R3 is independently, hydrogen or a saturated straight, cyclic or branched chain of an alkyl or alkenyl group containing 1 to 10 carbon atoms, and wherein the feed composition or feed additive further comprises at least one additional active substance selected from the group consisting of diallyl disulfide, garlic oil, allyl isothiocyanate, deoxycholic acid, chenodeoxycholic acid and derivatives thereof.

* * * * *